United States Patent [19]

Lotsof

[11] Patent Number: 4,857,523
[45] Date of Patent: Aug. 15, 1989

[54] RAPID METHOD FOR ATTENUATING THE ALCOHOL DEPENDENCY SYNDROME

[75] Inventor: Howard S. Lotsof, Staten Island, N.Y.

[73] Assignee: NDA International, Inc., Staten Island, N.Y.

[21] Appl. No.: 221,030

[22] Filed: Jul. 18, 1988

[51] Int. Cl.$^4$ ............................................. A61U 31/55
[52] U.S. Cl. .................................................. 514/214
[58] Field of Search ........................................ 514/214

[56] References Cited

U.S. PATENT DOCUMENTS

| | | | |
|---|---|---|---|
| 2,817,623 | 12/1957 | Schneider | 167/67 |
| 3,557,126 | 1/1971 | Sallay | 260/293 |
| 4,499,096 | 2/1985 | Lotsof | 514/214 |
| 4,587,243 | 5/1986 | Lolsol | 514/214 |

FOREIGN PATENT DOCUMENTS 1902227  6/1969  Fed. Rep. of Germany .

OTHER PUBLICATIONS

E. C. Sonay, Substance Abuse Disorder in Clinical Practice, 1983, pp. 31–59.
B. Tabakof, P. B. Sutker, C. L. Randall, Medical and Social Aspects of Alcohol Abuse, 1983, pp. 187–220.
G. R. Baumgartner, R. C. Rowen, Clonidine vs. Chlordiazepoxide in the Management . . . , Arch. Intern. Medicine 147, 1987, pp. 1223–1226.

Primary Examiner—Stanley J. Friedman
Attorney, Agent, or Firm—Howard C. Miskin

[57] ABSTRACT

The administration to an alcohol dependent of ibogaine, ibogaine HCl or other non-toxic salts of ibogaine, an alkaloid of the family apocynaceae, has been discovered to unexpectedly diminish the physiological and psychological aspect of the alcohol dependency syndrome. A single treatment will be effective for about 6 months. The treatments consisted of the oral administration of ibogaine or its salts in dosage ranges of 4 mg/kg to 25 mg/kg. The minimum effective dose was 400 mgs. and dosage increases above 1200 mgs. were found to be for the most part unnecessary.

9 Claims, No Drawings

RAPID METHOD FOR ATTENUATING THE ALCOHOL DEPENDENCY SYNDROME

BACKGROUND OF THE INVENTION

The present invention relates generally to improvements in the treatment of alcohol dependency and abuse and it relates particularly to an improved method for attenuating the physiological an psychological aspects of the alcohol habituation.

Treatment procedures heretofore employed or proposed for the diminishment of the alcohol habituation syndrome as well as behavioral therapy including the administration of antidepressants and/or tranquilizers have been generally ineffective.

HISTORICAL BACKGROUND

Ibogaine is one of at least 12 alkoloids found in the Tabernanthe iboga shrub of West Africa. The indigenous peoples have used the drug as a ritual, ordeal or initiation potion in large dosages as a stimulant in smaller doses. One of the first European references to the drug was made by Professor Baillon on the Mar. 6, 1889 session of the Linnaen Society in Paris during which he described samples obtained by Griffon de Bellay from Gabon and the French Congo.

Early isolation and identification of ibogaine was accomplished by Dybowski and Landrin (Compt. rend. ac. sc. 133:748, 1901); Haller and Heckel (ibid. 133:850); Lambert and Heckel (ibid. 133:1236) and Landrin (Bull. sc. pharm. 11:1905).

Interest in the drug seemed to lie fallow until it was picked up by Raymond-Hamet and his associates Rothlin, E. and Raymond-Hamet published the "Effect Of Ibogaine On the Isolated Rabbit Uterus" in 1938 (Compt. rend. soc. biol. 127:592-4). Raymond-Hamet continued to study the drug for a period of 22 years. He singularly published 9 papers: Pharmacological Action Of Ibogaine (Arch. intern. pharmacodynamie, 63:27-39, 1939), Two Physiological Properties Common to Ibogaine And Cocaine (Compt. rend. soc. biol. 133:426-9, 1940), Ibogaine and Aphedrine (Ibid. 134: 541-4, 1940), Difference Between Physiological Action Of Ibogaine And That Of Cocaine (Ibid. 211:285-8, 1940), Mediate And Intermediate Effects Of Ibogaine On The Intestine (Compt. rend. soc. biol. 135 176-79, 1941), Pharmacologic Antagonism Of Ibogaine (Compt. rend. 212: 768-771, 1941), Some Color Reactions Of Ibogaine (Bull. soc. chim. Biol., 25: 205-10, 1943), Sympathicosthenic Action Of Ibogaine On The Vessels Of The Dog's Paw (Compt. rend. 223: 757-58, 1946), and Interpretation Of The Ultraviolet Absorption Curves Of Ibogaine And Tabernanthine (Ibid. 229: 1359-61, 1949).

Vincent, D. began his work on ibogaine by a collaboration with Sero, I.: Inhibiting Action Of Tabernanthe Iboga On Serum Cholinesterase (Compt. rend., Soc. Biol. 136: 612-14, 1942). Vincent participated in the publication of five other papers: The Ultraviolet Absorption Spectrum Of Ibogaine (Brustier, B., Vincent, D. & Sero, I., (Compt. rend., 216: 909-11, 1943), Detection of Cholinesterase Inhibiting Alkaloids (Vincent, D. & Beaujard, P., Ann. pharm. franc. 3: 22-26, 1945), The Cholinesterase of the Pancreas: Its Behavior In The Presence Of Some Inhibitors In Comparison With The Cholinesterases Of Serum And Brain (Vincent, D. & Lagreu, P., Bull. soc. chim. biol. 31: 1043-45, 1949); and two papers, which he and Raymond-Hamet worked on together: Action Of Some Sympathicosthenic Alkaloids On The Cholinesterases (Compt. rend. soc. biol., 150: 1384-1386, 1956) and On Some Pharmacological Effects Of Three Alkaloids Of Tabernanthe Iboga, Baillon: Ibogaine, Iboluteine And Tabernanthine (Compt. rend. soc. biol., 154: 2223-2227, 1960).

The structure of ibogaine was investigated by Dickel et al (J.A.C.S. 80, 123, 1958). The first total synthesis was cited by Buchi et al. (J.A.C.S. 87, 2073, 1965) and (J.A.C.S. 88, 3099, 1966).

In 1956 Salmoiraghi and Page elucidated ibogaine's relations to serotonin (J. Pharm & expt. ther. 120 (1), 20-25, 1957.9). About the same time J. A. Schneider published three important papers. The first, Potentiation Action Of Ibogaine On Morphine Analgesia was done in colloboration with Marie McArthur (Experiential 12: 323-324, 1956). The second was Neuropharmacological Studies Of Ibogaine: An Indole Alkaloid With Central Stimulant Properties (Schneider J. A. & Sigg, E. B. Annals of N.Y. acad, of sciences, Vol 66: 765-776, 1957) and third was An Analysis Of The Cardiovascular Action Of Ibogaine HCL (Schneider, J. A. & Rinehard, R. K., Arch. int. pharmacodyn., 110: 92-102, 1957).

Ibogaine's stimulant properties were further investigated by Chen and Bohner in A Study Of Central Nervous System Stimulants (J. Pharm. & Expt. Ther., 123 (3): 212-215, 1958). Gerson and Lang published A Psychological Study Of Some Indole Alkaloids (Arch. intern. pharmacodynamie, 135: 31-56, 1962).

R. D. Bunag, in 1963, evaluated certain aspects of the relationship between ibogaine and Substance P. (Bunag, R. D.; Walaszek, E. J. The Cardiovascular Effects of Substance P In The Chicken; Ann. N.Y. Acad. Sci. 104, Part 1, 437-48, 1963).

In 1969, Claudio Naranjo reported on the effects of both ibogaine and harmine on human subjects in his paper: Psychotherapeutic Possibilities Of New Fantasy-Enhancing Drugs (Clinical Toxicology, 2 (2: 209-224, June 1969).

Dahir, H. I., as his 1971 Doctoral thesis, published A Comparative Study Of The Toxicity Of Ibogaine and Serotonin (University Microfilm International 71-25-341, Ann Arbor, Mich.). The paper gives an overview of much of the work accomplished with ibogaine.

Additionally studies of interest include: The Effects Of Some Hullucinogens On Aggressiveness Of Mice And Rats (Kostowski et al., Pharmacology 7: 259-263, 1972), Cerebral Pharmacokinetics Of Tremor-Producing Harmala And Iboga Alkaloids (Zetler et al., Pharmacology 7 (4): 237-248, 1972), High Affinity 3H-Serotonin Binding To Caudate: Inhibition By Hallucinogenis And Serotonergic Drugs (Whitaker, P. & Seeman, P., Psychoparmacology 59: 1-5, 1978, Biochemistry), Selective Labeling Of Serotonin Receptors by d-(3H) Lysergic Acid Diethylamide In Calf Caudate (Proc. natl. acad. sci., USA, Vol. 75, No. 12, 5783-5787, December 1978, Biochemistry) and A Common Mechanism Of Lysergic Acid, Indolealkylamine And Phenthylamine Hallucinogens: Serotonergic Mediation Of Behavorial Effects In Rats (Sloviter, Robert et al, J. Pharm. & Expt. Ther., 214 (2): 231-238, 1980).

SUMMARY OF THE INVENTION

It is a principal object of the present invention to provide an improved method for the treatment of alcohol dependency and abuse.

Another object of the present invention is to provide an improved method for lessening the physiological and psychological aspect of the alcohol habituation deprivation.

Still another object of the present invention is to provide a method of the above nature characterized by its high degree of success, the absence of the great pain and discomfort accompanying earlier treatments, the ease and convenience of application, the absence of undesirable or persistent side effects and the persistent effectiveness of the treatment.

The above and other object of the present invention will become apparent from a reading of the following description which sets forth preferred embodiments thereof.

A feature of the present invention is based on the discovery that an alkaloid of the family Apocynaceae and its therapeutically active derivatives and salts, particularly ibogaine and its therapeutically active, non-toxic derivatives and salts for example, ibogaine hydrochloride and other non-toxic salts of ibogaine, possess the unexpected unique ability to decrease alcohol consumption. Examples of other salts of ibogaine which may be used are ibogaine hydrobromide, and any other non-toxic salt of ibogaine.

For the purpose of definition, the alcohol abuse syndrome is meant to consist of all the symptomology demonstrated by users in their use of and search for alcohol.

A single treatment with ibogaine or ibogaine HCL of doses ranging from 4 mg/kg to 25 mg/kg administered orally reduced the use of alcohol in rats for at least forty days and in man for six months.

A treatment lasts about thirty hours during which time ibogaine exerts a stimulant effect. Apparently, an abreactive process is involved during ibogaine therapy but is not noticeable until the patient wakes from natural sleep occurring after primary and secondary effects of ibogaine are diminished. When effective, ibogaine left the abuser with a diminished desire to use alcohol and no noticeable signs of physical or psychological withdrawal. Subjects appear relaxed, coherent, with a sense of direction and feelings of confidence.

Ibogaine was one of five substances studied. The other four—mescaline, psilocybin, LSD and DMT though different in duration of action and intensity—have similar psychotrophic effects that are well documented and will not be discussed here. Ibogaine, unlike the others, is not a euphoriant hallucinogen and did not leave the subjects open to swells of emotion. While under the influence of ibogaine, emotional responses to traumatic repressed thoughts and feelings appeared to be negated.

Another effect of ibogaine administration that was found interesting was that even after twenty-six to thirty hours of wakefulness, subjects slept three to four hours and awoke fully rested. This pattern continued, diminishing slowly, over a three to four month period.

The effects of oral administration of ibogaine are first noticed in fifteen to twenty minutes. Initially, a numbing of the skin is accompanied by an auditory buzzing or oscillating sound. Within twenty-five to thirty-five minutes the auditory transcends across the sensory mechanisms to include the visual: objects appear to vibrate with great intensity. It is at this time that the dream enhancement or anti-mnemonic repression effects begin. In many cases an accute stage of naseau follows the dreamlike visualization. The visions end abruptly and the numbness of the skin begins to abate.

This is followed by six to eight hours of a high energy state during which the subjects see "lightening" or flashes of light dance about them. Thoughts which seem to amplify the meaning of the visual material seen during the primary phase of ibogaine intoxication continue during this period.

Between twenty-six and thirty-six hours, the level of stimulation diminishes and the test subject falls asleep.

Thus, three stages of ibogaine intoxication have been observed. First, a waking state of dreamlike visualizations lasting for three to four hours occurs during which time the person receiving ibogaine manifests repressed material visually. Second, a high energy period accompanied by flashes of light, the appearance of a vibration to all objects, and the awareness of thoughts appropriate to the visual material seen previously by the subject. Third, a diminishing energy period free of vibration or light flashes and culminating in sleep.

In the administration of acceptable dosage forms, any one of a variety of preparations may be compounded, for example: capsules, tablets, pills, powder, solutions, etc. In addition to the active agent, there may be present additional substances used in the manufacture of pharmaceutical preparations such as binders, fillers and other inert ingredients.

There are a number of mechanisms and relationships of action by which ibogaine may attenuate the alcohol abuse syndrome. These include memory coding by RNA and protein, immune mechanisms, neurohormonal adaptions, involvement in systems including catecholamines, acetylcholine, serotonin, adrenergis compounds, hypothalmic-pituitary neuro-hormones, as well as adaptations taking place outside the central nervous system. The mode of action may also include structure-activity relationships, receptor within the brain or other binding sites, psychological causes, systems involving vaspopressin, prostaglandins, testosterone, adrenal steroids, metabolic imbalances, prevention of access of alcohol to the site of action, or occupation and saturation of receptor sites as well as interaction with systems involving Substance P.

While the exact mechanism or mechanisms of action by which ibogaine attenuates the alcohol dependency and abuse syndrome is not clear, it is known that it functions by interaction with one or more of the above systems. It is not intended, however, that the present invention be limited to any particular theory or mechanism of action.

The advantage of this invention is that it allows for the rapid diminishment of physiological and psychological withdrawal and the attenuation of the subject's desire to use alcohol for about six months. The invention itself is non-addicting, and in a series of treatments will remove any potential for its own abuse.

The following examples are given by way of illustration of the present improved method of treating alcohol abuse and dependency and are not intended to limit the scope of the present invention.

Male Long-Evens rats weighing approximately 350 to 400 grams were used in this experiment. Each animal was drinking at least 2.5g/kg of 10% ethanol (EtOH) per day. Ibogaine HCl (60 mg/kg) was administered by gavage to each of the rats, daily for five days. The rats always had access to a choice of either EtOH or water.

The dose of 60 mg/kg of ibogaine was dissolved in 0.9% saline solution. The dose was determined by the physical characteristics demonstrated in man with doses that proved efficacious for the interruption of heroin and cocaine dependency: ataxia and a tendency for the subject to lay down (U.S. Pat. Nos. 4,499,096 and 4,587,243). The dose was then reduced so that there were no signs of ataxia, tremor or other symptoms of toxicity or debilitation.

Weight gain was normal indicating normal food consumption and water intake did not change much except during the five day period of treatment when it was erratic.

Seven rats in all were used in this experiment. One rat showed a 13% to 17% increase in drinking and one rat showed no mean percentage change over the course of the experiment thus to an extent duplicating the percent of efficacy shown in the interruption of heroin dependency, though in the case of heroin dependency, cessation of the use of heroin was complete in the five out of seven subjects and not, only diminished.

The substantial drop in ethanol consumption exhibited during the ibogaine treatment period was excluded from the 30 and 40 day averages of alcohol consumption as was the data from the expected rebound phenomena or alcohol deprivation effect during which alcohol consumption increased immediately following the termination of ibogaine administration. Alcohol intake is given as ml/day.

EXAMPLE 1

A rat weighing 388 grams was drinking an average of 17 ml of 10% ethanol per day. During the five days of ibogaine treatment, alcohol consumption was reduced to 12 ml demonstrating a reduction of 29 percent. Evaluation of average ethanol use for both 30 day and 40 day averages each showed intake at 11 ml or a reduction under baseline consumption of 35 percent.

EXAMPLE 2

A rat weighing 370 grams was drinking an average of 16 ml of 10% ethanol per day. Ethanol consumption decreased to an average of 10.5 ml during ibogaine treatment (34% reduction). The average over the first 30 days was 11 ml ethanol consumption (31% reduction) and the average over the first 40 days of ethanol consumption was 10 ml (37% reduction).

EXAMPLE 3

A rat weighing 390 grams was drinking an average of 32 ml of ethanol before treatment with ibogaine. During ibogaine treatment ethanol consumption dropped to 6.5 ml (80% reduction). Alcohol consumption over the first 30 days averaged 15 ml (53% reduction) and 17. ml over the 40 day period (45% reduction).

EXAMPLE 4

A rat weighing 398 grams was drinking an average of 18 ml of ethanol before ibogaine treatment. Ethanol consumption was reduced to an average of 6.5 ml of ethanol (64% reduction) during ibogaine treatment. Ethanol consumption during the 30 day period was maintained at 6.5 ml (64% reduction) and rose to 7 ml average over the 40 day period (61% reduction).

EXAMPLE 5

A human subject, age 42, weight 142 pounds was treated for cocaine dependency. Subject's use of 5 grams to 7 grams of cocaine per week was immediately terminated by the administration of 15 mg/kg ibogaine HCl.

The subject also exhibited an alcohol consumption problem and was drinking an average of 3 liters vodka per week at home, three to five bottles of wine at home or with meals outside of the home as well as, an average of five mixed drinks a day.

The subject's alcohol consumption was reduced to 1 liter vodka at home. Wine consumption was replaced by an average consumption of 12 cans of beer a week and the number of mixed drinks was reduced to five or ten per week. This reduction was maintained for six months at which time we ceased to follow the subject's progress. This subject had demonstrated an alcohol consumption reduction of approximately sixty percent from a single treatment of ibogaine HCl.

It is anticipated that increased efficacy may be accomplished by the administration of a series of ibogaine treatment procedures for alcoholism, as a series of treatments has been shown to be additionally effective for the treatment of the narcotic and cocaine dependency syndromes in terms of length of duration of efficacy in maintaining freedom from drug self administration.

While there have been described preferred embodiments of the present invention, it is apparent that numerous alterations, omissions and additions may be made without departing from the spirit thereof.

I claim:

1. The method of treating alcohol dependency and abuse comprising internally administering to one dependent on and abusive of alcohol a dosage of between 4 mg and 25 mg per kg of weight of the abuser of ibogaine or a therapeutically active compound of ibogaine or a mixture thereof.

2. The method of claim 1 wherein said dosage is orally administered.

3. The method of claim 1 or 2 wherein said compound is a non-toxic salt of ibogaine.

4. The method of claim 1 or 2 wherein said dosage is ibogaine or one or more non-toxic salts of ibogaine or a mixture thereof.

5. The method of claim 3 or 4 wherein the administered dosage of said composition contains ibogaine or a non-toxic salt of ibogaine or a mixture thereof of between 400 mg and 1000 mg.

6. The method of claim 3 wherein said ibogaine is in the form of the hydrochloride or hydrobromide salt thereof.

7. The method of claim 4 wherein said dosage is in capsule, tablet, pill, powder or solution form.

8. The method of claim 4 wherein said dosage is admixed with binders or fillers.

9. The method of claims 3, 4 or 5 wherein a plurality of said dosages are administered, intervals of a plurality of days intervening between successive dosages.

* * * * *